United States Patent [19]

La Duca et al.

[11] Patent Number: 5,091,304
[45] Date of Patent: Feb. 25, 1992

[54] WHOLE BLOOD ACTIVATED PARTIAL THROMBOPLASTIN TIME TEST AND ASSOCIATED APPARATUS

[75] Inventors: Frank M. La Duca, East Brunswick; Eduardo I. Marcelino, Edison, both of N.J.

[73] Assignee: International Technidyne Corporation, Edison, N.J.

[21] Appl. No.: 396,043

[22] Filed: Aug. 21, 1989

[51] Int. Cl.$^5$ ............................................. C12Q 1/56
[52] U.S. Cl. ...................................... 435/13; 436/69; 436/79
[58] Field of Search ...................... 435/13; 436/69, 70, 436/79

[56] References Cited

U.S. PATENT DOCUMENTS 4,782,026 11/1988 Baugh et al. ......................... 436/69

Primary Examiner—Amelia Burgess Yarbrough
Attorney, Agent, or Firm—Arthur L. Plevy

[57] ABSTRACT

An activated partial thromboplastin time (APTT) test is described which does not require blood which has been anticoagulated with citrate. The test enables the citrate anticoagulant step to be combined with the contact activation step and hence enables one to employ fresh non-anticoagulated blood specimens to directly perform the APTT Test.

25 Claims, No Drawings

WHOLE BLOOD ACTIVATED PARTIAL THROMBOPLASTIN TIME TEST AND ASSOCIATED APPARATUS

BACKGROUND OF THE INVENTION

This invention relates to a clotting assay performed using freshly obtained, non-anticoagulated, blood and more particularly to a whole blood Activated Partial Thromboplastin Time (APPT) test which is performed using fresh non-citrated whole blood and specific reagents placed in a single test tube.

Fundamental to human lift and well being is the ability of human blood, in response to certain stimuli, to thicken and eventually form structures known as blood clots. Blood clotting occurs in response to both internal and external bleeding. Conversely, unwanted clot formation or blood thickening can have undesirable effects among which are circulatory blockages. Clinical occurrence of uncontrolled bleeding or clotting are corrected by therapeutic infusion of blood, blood products or medications. All therapies are monitored to determine efficacy by use of specific blood clotting assays.

Blood clotting is a process which involves three interacting components. These are the blood vessels, blood coagulation factors and blood platelets. The blood coagulation factors are proteins or glycoproteins which freely circulate within the body. In the clot formation process they interact in a mechanism commonly referred to as the coagulation cascade. In this process an inactive coagulation factor is chemically converted to an active enzyme. This enzyme subsequently converts another inactive enzyme precursor to an active state. The end result of these processes is the conversion of plasma soluble fibrinogen to fibrin, which is plasma insoluble. The fibrin clot is a crosslinked matrix which entraps the formed elements of the blood thereby sealing off the bleeding site. The formed elements consist of the platelets, white blood cells and red blood cells.

Platelets are cell fragments which play multiple roles in the clotting process. They initially attach to the exposed collagen matrix of broken blood vessels and to each other to form a primary platelet plug to seal off the bleeding site. During this aggregation the platelets release chemical components into the plasma which are important in the clotting process. One such component is called platelet factor 3 (PF3). Platelet factor 3 is a phospholipid which serves as a necessary cofactor in the coagulation cascade.

Specific blood clotting assays enable the clinician to determine the integrity of the blood coagulation cascade and the efficacy of therapy. One such clotting assay is the Partial Thromboplastin Time (PTT) test. This test was first described by Brinkhous and Langdell. See an article entitled "Newer Approaches To The Study Of Hemophilia & Hemophiloidal States" by K. M. Brinkhous et al, JAMA 154:481-486, 1954. See an article entitled "Effect of Antihemophilic Factor On One Stage Clotting Tests" by R. D. Langdell et al, J Lab Clin Med 41:637-647, 1953. The principle of the PTT is that citrated platelet poor (i.e., depleted) plasma (PPP) is added to a mixture containing platelet factor 3 (PF3) substitute and calcium. The PF3 substitute is a phospholipid derived from brain and lung tissue. See article entitled "A Brain Extract As A Substitute For Platelet Suspensions In The Thromboplastin Generation Test" by W. H. Bell and H. G. Alton, Nature 174:880-881, 1954. This substitutes for the role which platelets play in the clotting process. The calcium is required since the native calcium present in circulating blood has been rendered unusable by the addition of citrate. Calcium is a necessary component for clotting.

The PTT assay proved a valuable clinical test to evaluate the coagulation cascade. Its one major drawback was a relative lack of reproducibility among different individuals. This made it difficult to establish a range of normal values of the test and determine if a patient's value was within or outside of this normal range. With further research it was determined that much of this variability was attributable to the processes involved in the initial activation of the coagulation cascade. This "contact activation" sequence was found to be highly variable among individuals. By standardizing the rate at which this activation occurs, it was possible to greatly improve the reliability of the PTT assay. This standardization was accomplished by addition of an activator to the PTT mixture. The PTT conducted in the presence of this activator was first described by Proctor and Rapaport. See an article entitled "The Partial Thromboplastin Time With Kaolin" by R. P. Proctor et al, Am J Clin Path 36:212-219, 1961. This test is known as the Activated Partial Thromboplastin Time (APTT) test. The test employed the particulate activator kaolin and later studies demonstrated the use of a soluble plasma activator, ellagic acid. See an article entitled "Activation of Hageman Factor by Solutions of Ellagic Acid" by O. D. Ratnoff and J. D. Crum, J Lab Clin Med 63:359-377, 1964. The APTT assays currently used in the clinical laboratory are minor modifications of these earliest tests. See the chapter, "Recalcification Time Test And Its Modification (Partial Thromboplastin Time, Activated Partial Thromboplastin Time And Expanded Partial Thromboplastin Time", by C. Hougie, In the text Hematology, 3rd edition, ed Williams, McGraw Hill Book Co., N.Y., pg. 1662-1664, (1983).

By elimination of the variable nature of activation, the APTT test has proven a more reliable test than the earlier PTT. It is particularly useful in identification of clotting factor deficiencies, of which the most common are the Hemophilias—Hemophilia A (Factor VIII deficiency), Hemophilia B (Factor IX deficiency) and Hemophilia C (Factor XI deficiency). It is also valuable as means to monitor the effect of clot inhibiting agents such as heparin. Heparin is an animal derived substance which directly interferes with the formation of the fibrin clot and is used extensively to control clotting in patients predisposed to uncontrolled coagulation. Such patients are typically those having a recent myocardial infarction (i.e., heart attack), stroke or episode of thrombophlebitis (clots in the large blood vessels). Another group of patients that require heparin are those individuals who require extracorporeal circulation, i.e., heart bypass surgery or renal dialysis.

To date the APTT assay has been performed exclusively using citrated platelet poor plasma. Such blood is routinely obtained by hospital personnel and transported to a central laboratory where the test is performed. Such batch processing has proven economical and practical to screen large numbers of patient plasmas. However the same characteristics of the test which make it practical in this example render it unacceptable in a variety of clinical settings. For example in open heart surgery the delay of time between drawing the blood sample and obtaining the APTT result makes the test useless in control of therapy. To overcome these drawbacks a more practical test used in this setting is the Activated Clotting Time Test (ACT) (Hattersley, JAMA 196:150–154, 1966). Unlike the APTT this test is performed at the patient's bedside using native, or, non-anticoagulated (non-citrated) blood. Such an assay allows one to quickly assess the effect of heparin on the clotting mechanism and to alter the therapy appropriately. This test also allows one to measure the high levels of heparin used in these instances.

An obvious difference between the ACT and APTT is that clot formation proceeds in the ACT in the presence of plasma plus all blood elements. Scientists have advocated that such an analysis is more indicative of the patient's true coagulation state than clot inducing formation in plasma. Consequently, the APTT using whole blood has been proposed as a more sensitive and accurate measure of the coagulant state than the plasma based ACT (P. Hattersley, Heparin Anticoagulation, in the text Laboratory Hematology, ed. by J. Koepke, Churchill, Livingston, p. 789–818, 1984). In one such protocol the use of which has not been well documented, whole blood samples are collected from the patient and citrate anticoagulated. The blood is then transferred to a reaction vessel to which the APTT reagents and calcium is subsequently added. This two step process is necessary as a meaningful APTT test requires a period of contact activation which traditionally ranges from 2 to 5 minutes. In order to achieve uniformity of activation, the clotting process is inhibited by sequestering of calcium with citrate or unregulated coagulation will occur. The two step whole blood protocol is therefore essentially identical to the plasma APTT. In a second version non-anticoagulated blood is obtained from the patient to perform a bedside test. (J. Blakely, A Rapid Bedside Method For Control Of Heparin Therapy, Canad. Med. Assoc. J. 99:1072–1076, 1968). The non-citrated blood is mixed with activator and $PF_3$ substrate and the clotting time determined. The lack of citrate anticoagulation eliminates the ability to regulate the "contact activation" and this test, therefore, bears more resemblance to the ACT than the APTT.

The present invention relates to an APTT assay which does not require blood which has previously been anticoagulated with citrate. By combining the citrate anticoagulation step with the contact activation step an APTT assay is provided which uses fresh, non-anticoagulated blood specimens. Thus, the coagulant state in whole blood may be defined independently of the previous need to pre-collect blood in a special citrated tube.

The major distinguishing feature of the APTT test compared to its forefather, the PTT test, is that a protocol is followed which allows the blood to be in contact for a pre-established, standardized period of time with a blood coagulation activator. This period of "contact activation" is a time and temperature dependent process during which the coagulation cascade is initialized. In this manner, the time to formation of a clot, following the addition of calcium, is truly indicative of the integrity of the clotting state.

Since blood removed from the body has a natural tendency to clot, it is imperative that a substance be added to prevent uncontrolled coagulation. In order to properly perform the APTT test, blood must be anticoagulated so that the contact activation step may be properly performed.

Many substances have the inherent ability to prevent clotting such as heparin, dextran, EDTA or sodium oxylate. However the anticoagulant of choice is sodium citrate. This substance works exclusively by chelating the free calcium ions present in the blood. Without calcium, clotting cannot take place. The other anticoagulants are not used since they exert multiple effects which disrupt normal coagulation processes. The anticoagulant effect of citrate is easily reversed by addition of exogenous calcium. Calcium chloride is the salt commonly used. The present invention contains the step of citrate anticoagulation within a test container whereby an APTT assay may be performed at the patient bedside on non-anticoagulated whole blood specimens which are drawn directly from the patient. Consequently, the advantages of an immediate, bedside analysis of patient samples, which the ACT brought to open heart surgery are now available to the hospitalized community at large and to out patients in clinics and doctor's offices.

Prior to the development of the assay according to this invention, the APTT has been traditionally performed using citrated plasma. Though occasionally advocated for use with citrated whole blood, the test is rarely performed on this substrate and has not been clinically documented.

SUMMARY OF THE INVENTION

This invention describes a unique APTT test and a mixture of reagents employed in such a test. The test allows one to simultaneously combine citrate anticoagulation of the blood with contact activation of the clotting cascade. Through use of this invention it is now possible to collect blood samples and perform assays in a single test tube, eliminating the need to perform multiple transfers of blood and reagents. The technique enables one to perform an APTT analysis on freshly drawn, non-anticoagulated blood. Such APTT analysis was not available according to prior art techniques.

In preparation for performing the assay, sodium citrate as an anti-coagulant, diatomaceous earth as a blood coagulation activator and platelet factor substitute together with stabilizers and buffers are added to a test tube and freeze dried. The reagents may be combined and used in liquid form without freeze drying. By selecting the appropriate buffers one adds fresh blood to the mixture which serves to simultaneously (1) rehydrate the reagents, (2) anticoagulate the blood, (3) initiate contact activation, and (4) supply the necessary platelet factor substitute integral to the APTT test. After a pre-established incubation period (37° C.) calcium in the form of a salt is added back to initiate the clotting cascade. The length of time required to form a clot is measured using a suitable whole blood analyzer, for example the HEMOCHRON Coagulation Timer, see U.S. Pat. Nos. 3,836,333 and 3,695,842. The HEMOCHRON timer is a well known analyzer and is extensively employed in the field. The length of time required for the clot to form is related to the integrity of the clotting cascade.

Patient results which are outside a pre-established normal range are indicative of coagulation factor deficiency or the presence of an anticoagulant. One such anticoagulant is heparin. By careful monitoring of the patient's APTT results, the clinician may properly ascertain the integrity of the clotting system, diagnose deficient states or the presence of anticoagulants. An appropriate clinical course of patient management may then be formulated and monitored. The test is a whole blood activated partial thromboplastin time test (APTT) for the purpose of screening for clotting abnormalities and for maintaining of anticoagulant and procoagulant therapy.

DETAILED DESCRIPTION OF THE INVENTION

This invention encompasses the inclusion of a specific combination of reagents in a single test tube or test cartridge employed as a collection reservoir and the performance of the APTT assay in the same collection reservoir. The specific reagents include an anti-coagulant for blood anticoagulation, a coagulation activator for contact activation and platelet factor substitute to serve as the partial thromboplastin in the APTT assay. Sodium citrate is used to anitcoagulate blood to therefore prevent clotting. Sodium citrate, a salt of citric acid is the most common anticoagulant used in diagnostic coagulation tests. In any event, other citrate solutions, appropriate for coagulation procedures and often used in the collection of blood include citrate dextrose, citrate phosphate dextrose (CPD) and citric acid. The blood coagulation activator is used to initiate contact activation of the intrinsic blood coagulation cascade. Such activators may be employed as either particulate or soluble. The particulate activator employed is diatomaceous earth. Other particulate activators include Kaolin, celite, silica, micronized silica and as a soluble coagulation activator ellagic acid. A phospholipid is used as a platelet factor 3 substitute in the APTT assay. Platelet factor 3 substitute is normally required for clotting. The platelet factor 3 substitute may be derived from animal brain or lung tissue. See an article by Bell and Alton in *Nature* 174: pages 880–881, (1954). The process of extraction is an acetone-chloroform-methanol extraction of the demembraned brain tissue. These phospholipids may be obtained from a variety of animal sources such as human, bovine, ovine, goat or so on. The phospholipid used in the APTT is derived from bovine brain. Many samples of suitable phospholipids can be had by referring to a catalog provided by the Sigma Chemical Company of St. Louis, Missouri. This catalog lists a variety of phospholipid factors which may be obtained from many given brain tissues depending upon the processing procedure. The use of the phospholipid is extremely important.

As above indicated, calcium or calcium salts are employed for clot formation and such calcium salt is added after the blood is introduced into the collection reservoir anticoagulated and incubated. Calcium is required for clot formation of a citrated blood sample. The traditional calcium salt employed is calcium chloride. A number of other calcium salts would operate in lieu of calcium chloride. These are calcium chloride, calcium bromide, D-gluconic acid calcium salt and calcium phosphate. There are large numbers of calcium salts which also may be employed and these are listed in the Merck Index, ninth ed. Merck Company, Rahway, N.J. (1976). See pages 208–217 where various calcium salts are listed. Formulation of the reagent combination as the ingredients which are placed in the test reservoir or collection reservoir is as follows.

| Formulation of the reagent for the APTT | | |
|---|---|---|
| Component reagent | **preferred concentration (milligrams) | range of acceptable conc (milligrams) |
| diatomaceous earth | 4.5 mg. | 1.5–15 mg. |
| sodium citrate | 6.5 mg. | 4.5–8.4 mg. |
| phospholipid | .075 mg. | .03–3 mg. |
| barbital buffered saline comprising | | |
| sodium barbital | 1.76 mg. | .59–3.52 mg. |
| sodium chloride | 2.19 mg. | .73–4.38 |
| sodium azide | .75 mg. | 0–3.0 mg. |
| bovine albumin | .75 mg. | 0–4.5 mg. |
| calcium chloride | 2.36 mg. | 1.76 to 2.94 mg. |

**the preferred concentration is the one used in the current APTT test tube configuration. One adds 1.5 cc of blood to initial ingredients as listed above and then adds 0.5 cc of calcium chloride after incubation which is equivalent to 2.36 milligrams.

As indicated, the formulation as derived above may be in liquid form. It is the above formulation exclusive of the calcium chloride which is placed inside a test tube in liquid form and then freeze dried. Thus, the formulation is placed in liquid form in the test tube and the test tube is placed in a freeze drier. Here it is frozen for at least two hours or between 1 to 6 hours at a temperature of −40° C. After freezing the formulation, a vacuum is applied and heat supplied to the test tube and materials which elevates the temperature to about +12° C. to drive off water entrapped in the component formulation. The heating can occur at temperatures between 4°–16° C. for a period of about 15–18 hours. After this time, the various proteins and buffer solutes remain in a dried powdered state in the test tube and all water has been removed. The test tube is then stoppered under a partial vacuum. A suitable freeze drying apparatus is sold by the company designated as the Virtis Company of Gardiner, N.Y. and sold under the designation as Unitop 600. The unit is called a lyophilyzer and contains a 6 liter condenser. Condensers of lesser or greater volume may be used. The approach whereby the entire solution is freeze dried on the inside of a test tube is preferred. Since the test tube is stoppered as indicated above, one merely has to add whole blood to the tube either through the stopper by use of a syringe and needle or directly to the tube by removing the stopper. The tube is then incubated for a standard time and calcium is added and the time for blood clot formation from the time of the addition of calcium is determined. This will be explained in the examples to follow.

The collection reservoir or test tube may be one of several configurations depending on the clot detection device to be used. The following illustrates representative examples of suitable collection reservoirs and detection systems.

EXAMPLE 1

Manual Clot Detection Device

The assigned reagents (citrate, activator, phospholipid as well as stabilizers and buffers) are added to an evacuated or non-evacuated stoppered glass test tube. The amounts and processes were described above. The reagents are either lyophilized or in liquid form. The particulate activator may be celite, diatomaceous earth, kaolin, ellagic acid and other material as well although diatomaceous earth is used. The phospholipid is used as a platelet factor 3 substitute. Freshly drawn blood is added to the test tube. The test tube is agitated to ensure adequate mixing and placed in a 37° C. heat block or water bath for 3 minutes. After incubation calcium in the form of a calcium salt (calcium chloride) is added to initiate clotting. Using a manual tilt tube technique, the blood is inspected every 3-5 seconds until clot formation is observed. Upon formation of a sufficient clot, blood fails to move freely within the test tube upon tilting. This constitutes the end point of the test.

EXAMPLE 2

Hemochron Blood Coagulation Timer

The assigned reagents (citrate, activator, phospholipid) are added to a HEMOCHRON blood coagulation tube and lyophilized. Freshly drawn blood is added to the test tube. The test tube is agitated to ensure adequate mixing and placed in the test well of the HEMOCHRON model 400 or 800 blood coagulation time tester and the instrument started. After 3 minutes the tube is removed from the test well, calcium is added, the HEMOCHRON timer restarted and the test tube is returned to the HEMOCHRON test well. The time to detection of a formed clot is displayed on the timer. The principles of the HEMOCHRON detection system are outlined in detail in U.S. Pat. Nos. 3,695,842 and 3,836,333. Briefly, this detection mechanism consists of a magnetic detector positioned just below an inclined test tube containing the sample to be assayed. A cylindrical bar magnet within the tube remains in close proximity to this detector as the tube is slowly rotated about its axis of symmetry. When a fibrin mass forms, its adhesion to the magnet and to a plastic structure wedged into the tube causes the magnet to rotate with the tube. The magnet is thereby displaced from its initial position adjacent to the detector. A seconds timer, electrically connected to the magnet detector, displays the time interval between test initiation and the end point (as determined by displacement of the magnet).

The above-noted reagents and tests were employed to monitor heparin therapy. As indicated, a conventional APTT assay is performed using citrated plasma. The above-noted assay is performed using fresh non-anticoagulated blood. Typical performance characteristics are given in the table below.

Typical Performance Characteristics
The APTT is often used to monitor heparin therapy. The conventional APTT assay is performed using citrated plasma. The HEMOCHRON APTT is performed using fresh, non-anticoagulated blood. The typical times listed below (mean value ± standard deviation) demonstrate the normal range and the response to low or moderate heparin doses.

| Response Range | Heparin conc (units/ml) | HEMOCHRON APTT (secs) | Plasma APTT (secs) |
|---|---|---|---|
| normal range | 0 | 69 ± 8 | 29.4 ± 2.3 |
| low dose | 0.2 | 102 ± 17 | 44.0 ± 7.4 |
| heparin | 0.4 | 130 ± 18 | 74.9 ± 12.7 |
|  | 0.5 | 171 ± 17 | not recordable |
| high dose | 1.0 | 256 ± 33 | not recordable |
| heparin | 1.5 | 357 ± 58 | not recordable |

While typical blood collection reservoirs have been designated as test tubes and particularly the special type of test tube which is employed in the HEMOCHRON apparatus, one can, of course, utilize any other blood collection device to freeze dry or otherwise position the above-noted reagents thereon. For example, such devices may include a cuvette. The reagent can be placed inside a hypodermic syringe whereby blood would be drawn from the patient by the syringe needle and enters in the cavity associated with the needle where the freeze dried components would be placed on the cavity wall and so on.

It is, therefore, indicated that many different configurations can be employed for the blood collection device, all of which may include a blood collection reservoir and blood collection path. Hence the terms "blood collection device" or "blood collection or test reservoir" as employed herein generally describe such devices.

We claim:

1. A method for performing an activated partial thromboplastin time test (APTT) comprising the steps of:
    applying non-anticoagulated blood to a test reservoir containing effective amounts of an anticoagulant, a blood coagulation activator and a platelet factor substitute to enable said applied blood to simultaneously anticoagulate and initiate contact activation, wherein said anticoagulant is a citrate compound, said coagulation activator is either diatomeceous earth, kaolin, celite, silica, micronized silica, ellagic acid or a combination thereof and said platelet factor substitute is a phospholipid.
    incubating the mixture at a given temperature for a given period of time and then adding a sufficient amount of calcium to said mixture to initiate the clotting cascade,
    measuring the length of time required to form a blood clot in said test reservoir after the addition of said calcium.

2. The method according to claim 1 wherein the step of incubating includes placing the mixture in an environment having a temperature of 37° C. for a period of about three minutes.

3. The method according to claim 1, wherein said added calcium is calcium chloride.

4. The method according to claim 1 wherein said anticoagulant is sodium citrate.

5. The method according to claim 1 including the step of agitating the mixture prior to the step of incubating.

6. The method according to claim 1, wherein said added calcium is a calcium salt selected from calcium chloride, calcium bromide, D-gluconic acid calcium salt, calcium phosphate.

7. The method according to claim 1, wherein said activator is a particulate activator.

8. The method according to claim 1, wherein said activator is a soluble chemical activator, namely, tanning agents such as ellagic acid.

9. The method according to claim 1, wherein said platelet factor substitute is derived from bovine brain.

10. The method according to claim 1, wherein said platelet factor substitute is a phospholipid obtained from brain or lung tissue selected from human, bovine, ovine, goat or other animal brain or lung tissue.

11. A reagent combination used to perform an activated partial thromboplastin time (APTT) test which combination is placed in the blood containing reservoir of a blood collection device to which fresh blood is to be added, said combination comprising:
    a blood coagulation activator, an anticoagulant and a platelet factor substitute in effective amounts to simultaneously anticoagulate and initiate contact activation together with stabilizers and buffers, wherein said coagulation activator is a citrate compound, said platelet factor substitute is a phospholipid, said stabilizer is either sodium azide, albumin or a combination thereof, and said buffer is either sodium barbital, sodium chloride of a combination thereof.

12. The reagent according to claim 11, wherein said reagent is freeze dried as placed in said blood collection device.

13. The reagent according to claim 11, wherein said blood collection reservoir is a test tube.

14. The reagent according to claim 11, wherein said anticoagulant is sodium citrate.

15. The reagent according to claim 11, wherein said platelet factor substitute is a phospholipid derived from bovine brain tissue.

16. The reagent according to claim 11, wherein said stabilizers and buffers include a buffered saline solution, of sodium azide and albumin.

17. The reagent according to claim 16, wherein said buffered saline solution is barbital buffered saline comprising between 0.59 to 3.52 milligrams of sodium barbital and between 0.73 to 4.38 milligrams of sodium chloride for 1.5 cc of fresh blood to be used in said APPT test.

18. A reagent mixture used to perform an activated partial thromboplastin time (APTT) test which reagent mixture is placed in the blood containing reservoir of a blood collection device to which 1.5 cc of fresh blood is to be added comprising:

between 1.5 to 15 milligrams of a diatomeceous earth as a coagulation activator, between 4.5 to 8.4 milligrams of sodium citrate as an anticoagulant and between 0.03 to 0.3 milligrams of a phospholipid as a platelet factor substitute and suitable buffers and stabilizers, wherein said buffers are either sodium barbitol, sodium chloride or a combination thereof, and said stabilizers are either sodium azide, albumin or a combination thereof.

19. The reagent according to claim 18 including between 0.59 to 3.52 milligrams of sodium barbital and between 0.73 to 4.38 milligrams of sodium chloride as a buffer solution.

20. The reagent according to claim 19, further including between 0 to 3.0 milligrams of sodium azide and between 0 to 4.5 milligrams of albumin as stabilizers and preservative.

21. The reagent according to claim 20, further including adding between 1.76 to 2.94 milligrams of calcium chloride to said reagent and blood solution after a suitable incubation period to start said APPT test.

22. A method for performing an activated partial thromboplastin time (APPT) test comprising the steps of:

adding a predetermined amount of non-anticoagulated blood to a test reservoir containing a reagent mixture having between 1.5 to 15 milligrams of diatomaceous earth as a blood coagulation activator, between 4.5 to 8.4 milligrams of sodium citrate as an anticoagulant, between 0.03 to 0.3 milligrams of a phospholipid as a platelet factor substitute, between 0.59 to 3.52 milligrams of sodium barbital and between 0.73 to 4.38 milligrams of sodium chloride with said sodium barbital and chloride serving as a buffer, with 0 to 3.0 milligrams of sodium azide, with 0 to 4.5 milligrams of albumin, incubating said blood and reagent mixture at a temperature of 37° C. for a period between 2-5 minutes, adding between 1.76 to 2.94 milligrams of calcium chloride to said mixture after said period and, measuring the length of time required to form a blood clot in said mixture after adding said calcium chloride.

23. The method according to claim 22, wherein said predetermined amount of non-coagulated blood is 1.5 cubic centimeters of blood added to said reagent mixture having 4.5 milligrams of diatomaceous earth, 6.5 milligrams of sodium citrate, 0.075 milligrams of a phospholipid, 1.76 milligrams of sodium barbital, 2.19 milligrams of sodium chloride, with 0.75 milligrams of albumin, and 0.75 milligrams of sodium azide.

24. The method according to claim 23, wherein said albumin is bovine albumin.

25. The method according to claim 22, where the step of incubating the mixture at 37° C. is for a period of 3 minutes.

* * * * *